United States Patent [19]

Harvey et al.

[11] 4,425,324

[45] * Jan. 10, 1984

[54] HAZED TOOTHPASTE

[75] Inventors: Kenneth Harvey, Wilmslow; Stephen T. Connors, Sale, both of England; Eric Baines, Sydney, Australia

[73] Assignee: Colgate-Palmolive Company, New York, N.Y.

[*] Notice: The portion of the term of this patent subsequent to Oct. 26, 1999 has been disclaimed.

[21] Appl. No.: 407,222

[22] Filed: Aug. 11, 1982

Related U.S. Application Data

[63] Continuation-in-part of Ser. No. 262,013, May 11, 1981, Pat. No. 4,356,168.

[51] Int. Cl.$^3$ ............ A61K 9/16; A61K 9/18
[52] U.S. Cl. ........................... 424/52; 424/49; 424/57; 206/524.4
[58] Field of Search ............... 424/49–58; 206/524.4

[56] References Cited

U.S. PATENT DOCUMENTS

| | | | |
|---|---|---|---|
| 3,906,090 | 9/1975 | Colodney | 424/52 |
| 3,911,104 | 10/1975 | Harrison | 424/52 |
| 3,937,321 | 2/1976 | Delaney et al. | 424/49 |
| 3,946,108 | 3/1976 | Tomlinson et al. | 424/49 |
| 4,007,260 | 2/1977 | Kim | 424/52 |
| 4,036,949 | 7/1977 | Colodney | 424/52 |
| 4,118,471 | 10/1978 | Pensak | 424/52 |
| 4,141,969 | 2/1979 | Mitchell | 424/52 |
| 4,152,419 | 5/1979 | Pensak | 424/52 |
| 4,159,280 | 6/1979 | Wason | 424/52 |
| 4,264,579 | 4/1981 | Carr | 424/52 |
| 4,356,168 | 10/1982 | Harvey et al. | 424/52 |
| 4,357,317 | 11/1982 | Weyn et al. | 424/52 |

*Primary Examiner*—Shep K. Rose
*Attorney, Agent, or Firm*—Robert L. Stone; Murray M. Grill; Herbert S. Sylvester

[57] ABSTRACT

A hazed toothpaste which can effect dental remineralization and reduce caries formation. The toothpaste contains a binary fluorine-providing system which provides about 750–1225 ppm fluoride from sodium monofluorophosphate and about 50–1000 ppm fluorine from sodium fluoride and a synthetic precipitated siliceous polishing agent. The toothpaste is stabilized against gassing in an unlined aluminium tube by the presence of a dicalcium phosphate which exerts a hazing effect on the toothpaste. Dicalcium phosphate also reduces color fading when a water-soluble dye is present. Additional haze to permit opacification of the toothpaste may be introduced by the presence of an opacifying agent, such as titanium dioxide.

8 Claims, No Drawings

HAZED TOOTHPASTE

This application is a continuation-in-part of application Ser. No. 262,013 filed May 11, 1981, now U.S. Pat. No. 4,356,168, issued Oct. 26, 1982.

This invention relates to a hazed toothpaste which promotes oral hygiene and which is also stabilized against gassing in an unlined aluminium tube and against colour fading, should a water-soluble dye be present.

In the past, toothpastes have been used which contain a single flourine-providing agent such as sodium fluoride, stannous fluoride or sodium monofluorophosphate (it being understood that a minor part of commercial sodium monofluorophosphate includes sodium fluoride).

Recently, as in British Pat. No. 1,435,624 of Beecham Group and U.S. Pat. No. 4,152,419 of Colgate-Palmolive toothpastes for promoting oral hygiene have come to prominence which contain two separately added fluorine-providing agents (that is, a binary system) sodium fluoride and sodium monofluorophosphate.

In previous practice, synthetic precipitated siliceous material has been described in toothpastes containing a single fluorine-providing agent, such as sodium monofluorophosphate as a desirable polishing agent. Such polishing agent does tend to cause gassing when the fluorine-providing toothpaste is in an unlined aluminum tube. It has been proposed to overcome this by contacting the siliceous material with calcium, either by pretreatment or in situ. This has been described in U.S. Pat. No. 4,141,969 of Colgate-Palmolive and U.S. Pat. No. 4,159,280 of J. M. Huber.

It has been observed that in toothpaste containing a binary fluorine-providing system of sodium monofluorophosphate and sodium fluoride whether or not synthetic precipitated siliceous polishing agent is pretreated with calcium, gassing in an unlined aluminium tube occurs and colour fading occurs when a water-soluble dye is present.

It is an object of this invention to provide a toothpaste containing sodium fluoride and sodium monofluorophosphate with desirable soluble fluorine retention which promotes oral hygiene, for instance, by reducing caries formation and which can effect dental remineralization in which the toothpaste contains dicalcium phosphate which hazes the appearance of the toothpaste and stabilizes it against gassing when packaged in an unlined aluminium toothpaste tube and against colour fading when a water-soluble dye is present. Thus, the presence of dicalcium phosphate and/or ions provided therefrom stabilizes the toothpaste containing sodium fluoride and sodium monofluorophosphate.

According to the present invention a hazed toothpaste comprises a binary fluorine-providing system which provides about 750–1225 ppm fluorine from sodium monofluorophosphate and about 50–1000 ppm fluorine from sodium fluoride and about 15–40% by weight of a synthetic precipitated siliceous polishing agent wherein there is present about 0.1–2.5% by weight of dicalcium phosphate which provides a hazed appearance to the toothpaste and stabilizes it against gassing when packaged in an unlined toothpaste tube and against colour fading when the toothpaste contains a water-soluble non-toxic dyestuff.

Sodium monofluorophosphate is employed in amount to provide about 750–1225 ppm fluorine to the toothpaste. This corresponds to about 0.5–1% by weight of sodium monofluorophosphate in the toothpaste. The preferred amount is about 0.76–0.874% which provides about 1000–1150 ppm fluorine to the toothpaste.

Sodium monofluorophosphate, $Na_2PO_3F$, as commercially available may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of above 12%, preferably above 12.7%, a content of not more than 1.5%, preferably not more than 1.2% of free sodium fluoride; and a sodium monofluorophosphate content of at least 12%, preferably at least 12.1% all calculated as fluorine.

Sodium fluoride is separately added to provide an additional fluorine amount of about 50–1000 ppm (for example—50–500 ppm). This corresponds to about 0.01–0.1% of sodium fluoride. Thus, 50–100 ppm, corresponds to about 0.01–0.02% of sodium fluoride.

The polishing agent is a synthetic precipitated siliceous material which may be essentially silica. Preferably it contains up to about 1% by weight of alumina interbonded therein. Such polishing materials may also be considered to be aluminosilicates, particularly sodium aluminosilicates. Typical examples are described in U.S. Pat. No. 3,906,090 of Colgate-Palmolive and in U.S. Pat. Nos. 4,015,996, 4,105,757, and 4,122,160 of J. M. Huber. Examples of these materials are ZEO 49 and ZEO 49B of Huber and Tixosil 53 of Sifrance. The polishing agent is employed in amounts of about 15–40% by weight, preferably about 15–30% e.g. 15–20% or about 25–30%.

The toothpaste containing the synthetic precipitated siliceous polishing agent typically has the consistency of a gel. Since the polishing agent may have a refractive index close to that of the liquid vehicle of the toothpaste (e.g. glycerol and/or sorbitol and a minor amount of water), the toothpaste is typically essentially clear to translucent in the absence of a hazing or opacifying agent. In accordance with the present invention the toothpaste gel is made more hazy, that is, made less clear and more translucent to opaque with the inclusion of about 0.1–2.5% by weight of a hazing agent. Dicalcium phosphate, including dicalcium phosphate dihydrate and anhydrous dicalcium phosphate and mixtures thereof, is the hazing agent employed. Dicalcium phosphate modifies the polishing characteristics of the toothpaste. It also has a particularly marked effect, even in the minor hazing amount employed, in stabilizing the toothpaste against gassing when packaged in an unlined aluminium tube and in stabilizing the toothpaste against dye fading when a water soluble dyestuff is present. It is preferably present in amount of about 0.1–1% by weight, most preferably about 0.5–1%, typically about 0.5%.

In addition to dicalcium phosphate, haze to opacify the toothpaste may be increased by the presence of an additional opacifying agent, typically in amount of about 0.5–2% by weight. Typical opacifying agents include titanium dioxide and substantial equivalents thereof, such as zinc oxide. Titanium dioxide is preferred for inclusion in the toothpaste.

The liquid vehicle of the toothpaste preferably contains about 20–80% by weight of humectant such as glycerol, sorbitol, polyethylene glycol 600 and mixtures of humectants. A toothpaste typically contains about 20–30% by weight of glycerol and about 30–60% by weight of sorbitol (70% solution).

Water (free of association with other components such as sorbitol) may be present too in amounts of up to about 50% by weight, typically about 1–10% in a low water composition or about 15–40% in a higher water formulation. In the absence of hazing and opacifying agents, the low water toothpaste typically would be more translucent or transparent in appearance than the higher water toothpaste.

Further, in the absence of the dicalcium phosphate hazing agent the toothpaste containing the binary fluoride system and siliceous polishing agent is prone to form gas and be incompatible with an unlined aluminum tube. This is particularly marked when the water content is high, e.g. about about 25% by weight. However, it is observable even in low water toothpaste.

When a water-soluble non-toxic dyestuff is present, e.g. in amount of about 0.001–0.1% by weight, colour fading in the absence of dicalcium phosphate hazing agent visibly occurs in both the higher water and lower water toothpaste.

The toothpaste also typically includes a gelling agent such as the natural and synthetic gum and gumlike material e.g. Irish moss, gum tragcanth, sodium carboxymethylcellulose, polyvinylpyrrolidone, xanthan, guar gum, starch and mixtures thereof.

Sodium carboxymethyl cellulose is preferred. The gelling agent content is typically about 0.1–5% by weight preferably about 0.1–0.5%. The gelling effect can be supplemented with about 5–10% by weight preferably about 6.5–8%, e.g. about 7–8% of a filler such as pyrogenic silica or a silica aerogel. Zeosyl 200 of J. M. Huber is a desirable silica filler material. "Zeosyl" is a trademark.

Any suitable surface active or detersive material may be included in the toothpaste. Such compatible materials are desirable to provide additional detersive, foaming and antibacterial properties depending upon the specific type of surface active material and are selected similarly. These detergents are water-soluble compounds usually, and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulphate detergent (e.g. sodium coconut fatty acid monoglyceride monosulphate), higher alkyl sulphate (e.g. sodium lauryl sulphate), alkyl aryl sulphonate (e.g. sodium dodecyl benzene sulphonate), higher fatty acid esters of 1,2-dihydroxy propane sulphonate and the like.

Further surface active agents include the substantially saturated higher aliphatic acyl amides of lower aliphatic amino carboxylic acid compounds, such as those having 12 to 15 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however for optimum effects.

The amide compounds may be employed in the form of the free acid or preferably as the water soluble salts thereof, such as the alkali metal ammonium, amine and alkylolamine salts. Specific examples there of are sodium and potassium N-lauroyl, myristoyl and palmitoyl sarcosides, ammonium and ethanolamine N-lauroyl sarcoside, N-lauroyl sarcosine, and sodium N-lauroyl glycide and alanine.

The surface active agent is typically employed in amount of about 1–5% by weight, preferably about 1–3% sodium lauryl sulphate is preferred.

Any suitable flavouring or sweetening materials may be employed in formulating a flavour for the toothpaste of the present invention. Examples of suitable flavouring consitiuents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and sodium saccharine. Sodium saccharine is preferred. Flavor is typically present in amount of about 0.5–1.5% by weight, preferably about 1% and sweetener in amount of about 0.1–0.2%.

If desired visible particles of pearlescent flakes, such as titanium dioxide coated mica flakes, may be distributed in the toothpaste, typically in amount of about 0.1–0.3% by weight. Likewise, the toothpaste may be striped.

The toothpaste should have a pH practicable for use. A pH range of about 5 to 10 is particularly desirable. The pH may be adjusted as desired with appropriate acidic or alkaline materials such as citric acid sodium hydroxide. The reference to the pH is meant to be the pH determination directly on the toothpaste. Stabilizers such as sodium benzoate may be used.

The following examples are illustrative of the invention. All amounts are by weight unless otherwise specified.

EXAMPLE I

The following toothpastes are prepared and placed in unlined aluminium tubes:

| INGREDIENTS | PARTS | |
|---|---|---|
| | A | B |
| Glycerine | 25.00 | 25.00 |
| Sodium carboxymethyl cellulose | 1.00 | 1.00 |
| Sodium saccharin | 0.30 | 0.30 |
| Titanium dioxide | 0.01 | 0.01 |
| FD & C Blue No. 1 (1% solution) | 0.20 | 0.20 |
| Polyethylene Glycol 600 | 3.00 | 3.00 |
| Synthetic precipitated silica (ZEO 49*) | 28.00 | 28.00 |
| Dicalcium phosphate dihydrate | — | 0.50 |
| Sodium monofluorophosphate | 0.76 | 0.76 |
| Sodium fluoride | 0.10 | 0.10 |
| Sodium lauryl sulphate | 1.76 | 1.76 |
| Flavour | 0.65 | 0.65 |
| Deionized water | Q.S. to 100 | Q.S. to 100 |

*contains about 50 ppm of calcium

Each of toothpaste A and B is translucent, toothpaste B being hazier than toothpaste A due to the presence of dicalcium phosphate dihydrate. Upon aging for 1 month at 43° C., 4° C. and at room temperature, gas formation occurs in the tubes containing toothpaste A and the initial colour due to the dye undergoes fading. In the tubes at 43° C. and at room temperature the surface of the tubes are attacked, with actual explosion of the tube occuring with the one aged at 43° C. In the case of toothpaste B, no gassing, tube attack and dye fading are observed upon aging for 1 month at 43° C., 4° C. and room temperature.

EXAMPLE 2

The following translucent toothpaste is prepared and placed in unlined aluminum tubes:

| INGREDIENTS | PARTS |
| --- | --- |
| Glycerine | 25.00 |
| Sodium carboxymethyl cellulose | 0.26 |
| Sodium saccharin | 0.20 |
| Titanium dioxide | 0.015 |
| FD & C Blue No. 1 (1% solution) | 0.19 |
| Polyethylene glycol 600 | 3.00 |
| Synthetic precipitated silica (Tixosil 53)* | 17.00 |
| Silica filler (Zeosyl 200) | 7.00 |
| Sodium monofluorophosphate | 0.76 |
| Sodium fluoride | 0.10 |
| Sodium lauryl sulphate | 1.76 |
| Flavour | 1.00 |
| Deionized water | 3.00 |
| Sorbitol (70%) | Q.S. to 100 |

*contains about 600 ppm of calcium

This toothpaste upon aging for 3 months at 43° C., 4° C. and room temperature causes gas formation in the tube. Further the initial dye colour fades. Substantial instability is also observed at 1 month.

Similar instability occurs when Tixosil 53 is replaced by ZEO 49.

When 0.10 part of dicalcium phosphate dihydrate is incorporated into the toothpaste containing each of Tixosil 53 and Zeo 49, the products became hazier and upon aging remain stable in the tubes while retaining intensity of dye colouring.

The foregoing examples are illustrative and do not limit the scope of the invention.

We claim:

1. A hazed toothpaste packaged in an unlined aluminium toothpaste tube comprising a binary fluorine-providing system which provides about 750–1225 ppm fluorine from sodium monofluorophosphate and about 50–1000 ppm fluorine from sodium fluoride and about 15–40% by weight of a synthetic precipitated siliceous polishing agent wherein there is present about 0.1–2.5% by weight of dicalcium phosphate which provides a hazed appearance to the toothpaste and stabilizes it against gassing when packaged in an unlined aluminium toothpaste tube and against colour fading when the toothpaste contains a water-soluble non-toxic dyestuff.

2. The hazed toothpaste claimed in claim 1 wherein sodium monofluorophosphate provides about 1000–1150 ppm fluorine and sodium fluoride provides about 50–500 ppm fluorine.

3. The hazed toothpaste claimed in claim 1 wherein said siliceous polishing agent contains up to about 1% by weight of alumina interbonded therein.

4. The hazed toothpaste claimed in claim 1 wherein said siliceous polishing material is present in amount of about 15–20% by weight.

5. The hazed toothpaste claimed in claim 1 wherein said siliceous polishing material is present in amount of about 25–30% by weight.

6. The hazed toothpaste claimed in claim 1 wherein said dicalcium phosphate is dicalcium phosphate dihydrate.

7. The hazed toothpaste claimed in claim 1 wherein said dicalcium phosphate is present in amount of about 0.1–1% by weight.

8. The hazed toothpaste claimed in claim 1 wherein a non-toxic water soluble dye is present in amount of about 0.1–1% by weight.

* * * * *